US012379360B2

(12) United States Patent
Hou-Broutin et al.

(10) Patent No.: US 12,379,360 B2
(45) Date of Patent: Aug. 5, 2025

(54) DETECTION SYSTEM FOR AN ELECTRONIC NOSE ALLOWING A PHYSICOCHEMICAL CLASSIFICATION OF ODOURS AND ELECTRONIC NOSE COMPRISING SUCH A SYSTEM

(71) Applicants: COMMISSARIAT À L'ÉNERGIE ATOMIQUE ET AUX ÉNERGIES ALTERNATIVES, Paris (FR); ARYBALLE, Grenoble (FR); CENTRE NATIONAL DE LA RECHERCHE SCIENTIFIQUE, Paris (FR)

(72) Inventors: Yanxia Hou-Broutin, Grenoble (FR); Sophie Brenet, Grenoble (FR); Arnaud Buhot, Grenoble (FR); Thierry Livache, Grenoble (FR); Cyril Herrier, Grenoble (FR); Tristan Rousselle, Grenoble (FR)

(73) Assignees: COMMISSARIAT À L'ÉNERGIE ATOMIQUE ET AUX ÉNERGIES ALTERNATIVES, Paris (FR); ARYBALLE, Paris (FR)

( * ) Notice: Subject to any disclaimer, the term of this patent is extended or adjusted under 35 U.S.C. 154(b) by 878 days.

(21) Appl. No.: 17/626,097

(22) PCT Filed: Jul. 8, 2020

(86) PCT No.: PCT/FR2020/051212
§ 371 (c)(1),
(2) Date: Jan. 10, 2022

(87) PCT Pub. No.: WO2021/009440
PCT Pub. Date: Jan. 21, 2021

(65) Prior Publication Data
US 2022/0252564 A1    Aug. 11, 2022

(30) Foreign Application Priority Data

Jul. 12, 2019 (FR) .................................... 1907884

(51) Int. Cl.
*G01N 33/00* (2006.01)
*G01N 33/543* (2006.01)

(52) U.S. Cl.
CPC ..... *G01N 33/0031* (2013.01); *G01N 33/0073* (2013.01); *G01N 33/54373* (2013.01); *G01N 2610/00* (2013.01)

(58) Field of Classification Search
CPC .......... G01N 2610/00; G01N 33/0031; G01N 33/0073; G01N 33/54373
See application file for complete search history.

(56) References Cited

U.S. PATENT DOCUMENTS

2015/0037909 A1* 2/2015 Livache ........... G01N 33/54373
422/69
2020/0256793 A1 8/2020 Hou-Broutin et al.

OTHER PUBLICATIONS

International Search Report for PCT/FR2020/051212 dated Nov. 11, 2020.

(Continued)

*Primary Examiner* — Jennifer Wecker
*Assistant Examiner* — Jonathan Bortoli
(74) *Attorney, Agent, or Firm* — Chrisman Gallo Tochtrop LLC (57) ABSTRACT

A detection system for an electronic nose which allows a physicochemical classification of odors, that is to say a classification as a function of the physicochemical properties of the volatile compounds, or odorous molecules, making up these odors. This detection system comprises sensors with cross-reactivity with respect to volatile compounds, each sensor comprising a sensitive part functionalized by a receptor comprising a sequence formed by the repetition of an (Continued)

| α-amino acid | 1-letter code | Hydrophobicity index | pI | Mr |
|---|---|---|---|---|
| Glycine | G | 0.48 | 5.97 | 75 |
| Alanine | A | 0.62 | 6.01 | 89 |
| Valine | V | 1.08 | 5.97 | 117 |
| Leucine | L | 1.06 | 5.98 | 131 |
| Isoleucine | I | 1.38 | 6.02 | 131 |
| Proline | P | 0.12 | 6.48 | 115 |
| Phenylalanine | F | 1.19 | 5.48 | 165 |
| Tyrosine | Y | 0.26 | 5.66 | 181 |
| Tryptophan | W | 0.81 | 5.89 | 204 |
| Serine | S | -0.18 | 5.68 | 105 |
| Threonine | T | -0.05 | 5.87 | 119 |
| Cysteine | C | 0.29 | 5.07 | 121 |
| Methionine | M | 0.64 | 5.74 | 149 |
| Asparagine | N | -0.78 | 5.41 | 132 |
| Glutamine | Q | -0.85 | 5.65 | 146 |
| Aspartic acid | D | -0.90 | 2.77 | 133 |
| Glutamic acid | E | -0.74 | 3.22 | 147 |
| Lysine | K | -1.5 | 9.74 | 146 |
| Arginine | R | -2.53 | 10.76 | 174 |
| Histidine | H | -0.40 | 7.59 | 155 |

α-amino acid. The α-amino acid of the receptor of a sensor of a first series of sensors is hydrophilic, while the α-amino acid of the receptor of another sensor of the first series is hydrophobic, and the α-amino acids of the receptors of two sensors of a second series of sensors have isoelectric points which differ from one another by at least one pH unit.

18 Claims, 4 Drawing Sheets

(56) References Cited

OTHER PUBLICATIONS

Lim, Jong Hyun et al. "A peptide receptor-based bioelectronic nose for the real-time determination of seafood quality" Biosensors and Bioelectronics, Aug. 3, 2012, vol. 39, No. 1, pp. 244-249.

Del Carlo, M. et al. "Novel oligopeptides based e-nose for food quality control: application to extra-virgin olive samples" Quality Assurance and Safety of Crops & Foods, Jun. 17, 2014, vol. 6, No. 3, pp. 309-317.

Beardslee, L.A. et al. "Selectivity Enhancement Strategy for Cantilever-Based Gas-Phase VOC Sensors Through Use of Peptide-Functionalized Carbon Nanotubes" Proceedings of the IEEE International Conference on the Micro Electro Mechanical Systems (MEMS) 2011, pp. 964-967.

Compagnone, D. et al. "Gold nanoparticles-peptide based gas sensor arrays for the detection of food aromas", Biosensors and Bioelectronics 2013, vol. 42, pp. 618-625.

Brenet, Sophie. et al. "Highly-Selective Optoelectronic Nose Based on Surface Plasmon Resonance Imaging for Sensing Volatile Organic Compounds", Analytical Chemistry 2018, vol. 90, pp. 9879-9887.

Sweet, R.M. et al. "Correlation of Sequence Hydrophobicities Measures Similarity in Three-dimensional Protein Structure", J. Mol. Biol. 1983, vol. 171, pp. 479-488.

Nelson, David L. et al. "Lehninger Principles of Biochemisty" Chapter 3, 4th edition, 2004.

Loufti, Amy et al. "Electronic noses for food quality: A review", Journal of Food Engineering 2015, vol. 14, pp. 103-111.

Specification and drawings for U.S. Appl. No. 17/442,201 entitled "Method for determining a potential poisoning of a sensor of an electronic nose by a volatile compound".

* cited by examiner

| α-amino acid | 1-letter code | Hydrophobicity index | pI | Mr |
|---|---|---|---|---|
| Glycine | G | 0.48 | 5.97 | 75 |
| Alanine | A | 0.62 | 6.01 | 89 |
| Valine | V | 1.08 | 5.97 | 117 |
| Leucine | L | 1.06 | 5.98 | 131 |
| Isoleucine | I | 1.38 | 6.02 | 131 |
| Proline | P | 0.12 | 6.48 | 115 |
| Phenylalanine | F | 1.19 | 5.48 | 165 |
| Tyrosine | Y | 0.26 | 5.66 | 181 |
| Tryptophan | W | 0.81 | 5.89 | 204 |
| Serine | S | -0.18 | 5.68 | 105 |
| Threonine | T | -0.05 | 5.87 | 119 |
| Cysteine | C | 0.29 | 5.07 | 121 |
| Methionine | M | 0.64 | 5.74 | 149 |
| Asparagine | N | -0.78 | 5.41 | 132 |
| Glutamine | Q | -0.85 | 5.65 | 146 |
| Aspartic acid | D | -0.90 | 2.77 | 133 |
| Glutamic acid | E | -0.74 | 3.22 | 147 |
| Lysine | K | -1.5 | 9.74 | 146 |
| Arginine | R | -2.53 | 10.76 | 174 |
| Histidine | H | -0.40 | 7.59 | 155 |

DETECTION SYSTEM FOR AN ELECTRONIC NOSE ALLOWING A PHYSICOCHEMICAL CLASSIFICATION OF ODOURS AND ELECTRONIC NOSE COMPRISING SUCH A SYSTEM

CROSS-REFERENCE TO RELATED APPLICATIONS

This is a National Stage application of PCT international application PCT/FR2020/051212, filed on Jul. 8, 2020, which claims the priority of French Patent Application No. 1907884, filed Jul. 12, 2019, both of which are incorporated herein by reference in their entirety.

TECHNICAL FIELD

The invention relates to the field of electronic noses.

More specifically, the invention relates to a detection system for an electronic nose which allows a physicochemical classification of odours, that is to say depending on the physicochemical properties of the volatile compounds, or odorous molecules, which compose these odours.

It also relates to an electronic nose comprising such a detection system.

The invention has many applications and, in particular, in:
the health field, for example to offer a substitute for smell to people suffering from a loss of smell, partial (hyposmia) or total (anosmia), or to diagnose or follow the evolution of diseases which are accompanied by the presence of volatile odorous compounds in biological fluids or in the breath, such as diabetes, certain cancers (prostate cancer, lung cancer, ovarian cancer, etc.) and certain microbial infections;
the food, cosmetic and pharmaceutical industries, for example to detect possible contamination in the manufacturing and/or distribution chains or to perform quality controls on raw materials or finished products;
the field of aromas and fragrances;
the field of safety of property and people, for example to monitor sites manufacturing, storing, handling and/or likely to be contaminated by potentially dangerous volatile materials, to detect the presence of dangerous substances such as explosives or toxic agents, or illicit substances such as narcotics, or else to search for people buried under rubble or debris; and
the field of the environment, for example to monitor the air quality or more or less confined atmospheres, or to monitor and analyse olfactory pollution of industrial or agricultural origin.

State of the Prior Art

Olfaction, or smell, is the sense with which mammals and in particular, humans, are provided and which allows them to detect and analyse the volatile compounds present in a gaseous medium and, in particular, the ambient air.

Today, there is a great demand for portable instruments which are able to mimic olfaction. These instruments are called electronic noses.

In addition to the fact that the detection of volatile compounds by an electronic nose must be fast and reliable, it must also be versatile, that is to say cover as many volatile compounds as possible. The objective is not to carry out an analysis of the gaseous medium volatile compound by volatile compound, but to carry out a discrimination between the volatile compounds present in this medium which is sufficiently fine to allow differentiating odours of very similar chemical compositions.

Today, being able to mimic olfaction still represents a scientific and technological challenge because olfaction is a very complex sense that combines biology, physicochemistry and cognition. This sense has remained little studied for a long time and its functioning little known.

In 1991, L. Buck and R. Axel have succeeded, for the first time, in identifying and sequencing genes for olfactive receptors (or OR). Their work has allowed establishing a general mechanism of functioning of the olfaction.

Unlike the interaction models usually encountered in biology, the detection and the identification of volatile compounds by ORs does not only rely on the key-lock model (model in which a biologically active molecule is recognised by a ligand which is specific thereto, for example an antibody if the biologically active molecule is an antigen) but is also based on the principle of a cross-reactivity where:
each OR can recognise several volatile compounds with different affinities;
each volatile compound can interact physicochemically with several ORs; and
different volatile compounds are recognised by different combinations of all ORs.

It was therefore by drawing inspiration from the biological mechanisms of the olfaction that electronic noses were designed.

Like its biological analogue, an electronic nose mainly consists of three systems, namely:
(1) a fluid system for transporting a sample of the gaseous medium between the outside of the electronic nose and the inside of that nose, this system acting as the respiratory system;
(2) a detection system which comprises an array of sensors (that is to say unit detection elements) with cross-reactivity relative to the volatile compounds present in the gaseous sample, the sensors acting as ORs of the human nose; and
(3) a computer system for processing and analysing the responses emitted by the sensors in the form of signals, this system acting as the human brain.

During the last three decades, the development of electronic noses has seen great progress with the use of various materials to constitute the sensitive part of the sensors (that is to say the part of the sensors which interacts physicochemically with the volatile compounds) and various transduction methods (that is to say allowing converting the physicochemical interactions occurring between the sensitive part of the sensors and the volatile compounds into usable signals).

However, the performance of these electronic noses is still much lower than that of the human nose, in particular in terms of the ability to differentiate the odours of similar chemical composition.

In most existing electronic noses, the sensitive part of the sensors, that is to say that which interacts with the volatile compounds, consists of non-biological materials such as semi-conductive metal oxides (or MOS) and semiconducting polymers. These materials generally have a high sensitivity but, due to the low variability of their physicochemical properties, the mechanisms by which they interact with the volatile compounds (which are mainly of the physical adsorption type in the case of MOS, and of the Van der Waals interaction and physical adsorption type in the case of semiconducting polymers) are too limited to allow an odour discrimination. In addition, the MOS have the drawback of having a high operating temperature (in the range of 200° C.

to 300° C.) while the semiconducting polymers are sensitive to air humidity, which affects the reproducibility of the detection.

In order to make electronic noses more efficient, it has been proposed to make the sensitive part of the sensors with organic molecules, which are biological or not, of low molecular weight, with various physicochemical properties, which are easily synthesised and which can, if possible, be self-assembled by surface engineering so as to obtain thin films, of nanometric thickness, with reproducible functionalisations.

This is how it was proposed to use:
alkane molecules terminated by various chemical groups (aromatic groups, carboxylic acids, esters, etc.), these molecules being deposited on carbon nanotubes, silicon nanowires or gold nanoparticles;
oligonucleotides attached to carbon nanotubes, graphene and graphene nanocrystals; and
peptides.

Concerning peptides, mention may be made of the works of L. A. Beardslee et al. (*Proceedings of the IEEE International Conference on the Micro Electro Mechanical Systems* (*MEMS*) 2011, 964-967, hereinafter reference [1]) which have used, in resonant cantilever sensors, three peptides each formed of 23 α-amino acids and a portion of which is used to immobilise these peptides on carbon nanotubes while another portion is intended to interact with volatile compounds. The latter is composed of an α-amino acid repeated 7 times, this α-amino acid being arginine in the first peptide, histidine in the second and threonine in the third. These three α-amino acids being polar and the sensors being exposed to ethanol and toluene, these authors show that the peptides and, in particular, that including 8 threonine residues have a greater affinity for ethanol, which is itself polar, as for toluene which is apolar. They conclude therefrom that by using suitable peptide functionalisation, it should be possible to modulate the affinity of the sensors relative to volatile compounds depending on the polarity of these compounds. However, they do not specify what this adapted functionalisation could be.

Mention may also be made of the works of D. Compagnone et al. (*Biosensors and Bioelectronics* 2013, 42, 618-625, hereinafter reference [2]) who have built an array of sensors based on gold nanoparticles functionalised by thioglycolic acid, glutathione, cysteine and three peptides including two dipeptides (γ-glutamylcysteine and cysteinylglycine) and a hexapeptide. Although of different lengths, these three peptides have similar physicochemical properties because they are structurally related to glutathione.

Finally, mention should be made of the works of S. Brenet et al. (*Analytical Chemistry* 2018, 90, 9879-9887, hereinafter reference [3]) which show that an array of sensors whose sensitive parts are functionalised by receptors consisting of biomimetic peptides and thiolated molecules with different physicochemical properties can discriminately recognise volatile compounds belonging to different chemical classes (alcohols, esters, carboxylic acids, ketones, hydrocarbons, aldehydes and amines), thus offering the possibility of making a differentiation of these compounds without a physicochemical scale.

However, it turns out that this reference is completely silent on both the chemical composition of the biomimetic peptides and the thiolated molecules forming the receptors and that, consequently, it does not allow knowing on which physicochemical base(s) the differentiation of volatile compounds is obtained.

DISCLOSURE OF THE INVENTION

The invention aims at overcoming the shortcomings of the state of the art by proposing a detection system for an electronic nose which is capable of detecting and identifying a set E of volatile compounds likely to be present in a gaseous sample and which allows a physicochemical classification of these volatile compounds depending on their physicochemical properties.

This detection system comprises a plurality of sensors with cross-reactivity relative to the volatile compounds of the set E, each sensor comprising a sensitive part disposed on a substrate and functionalised by a receptor whose physicochemical interaction with at least one of the volatile compounds of the set E produces a detectable signal, and is characterised in that:

it comprises n sensors, n being an integer greater than or equal to 3, the sensitive part is functionalised by a receptor of general formula (I):

$$X\text{-}(Esp)_m\text{-}Z \qquad (I)$$

wherein:
X represents a functional group ensuring an immobilisation of the receptor on the surface of the substrate or the residue of a compound comprising such a group,
m is equal to 0 or 1,
Esp represents a spacer arm, and
Z represents a sequence formed by the repetition of an α-amino acid;
the α-amino acid of the receptor of a sensor of a first series of sensors is hydrophilic while the α-amino acid of the receptor of another sensor of the first series is hydrophobic;
the α-amino acids of the receptors of two sensors of a second series of sensors have isoelectric points, respectively pI1 and pI2, which differ from each other by at least one pH unit, at least one of these two sensors not belonging to the first series.

Thus, according to the invention, a physicochemical classification of the volatile compounds is obtained depending on at least two of their physicochemical properties, namely: on the one hand, their hydrophilic or hydrophobic character and, on the other hand, their acid, neutral or base character, and this, by providing the electronic nose detection system with at least three sensors whose sensitive parts are each functionalised by a receptor comprising a sequence formed by the repetition of an α-amino acid and by choosing the α-amino acid of each sequence so that:

the α-amino acid of the receptor of a first sensor—which will be called sensor C1 in what follows—is hydrophilic while the an α-amino acid of the receptor of a second sensor—which will be called sensor C2 in what follows—is hydrophobic; and
the α-amino acids of the receptors of two sensors have isoelectric points which differ from each other by at least one pH unit, one of these two sensors can be the sensor C1 or the sensor C2, but the other of these sensors being a sensor different from the sensors C1 and C2.

In other words, the electronic nose detection system comprises at least:
either three sensors, respectively sensors C1, C2 and C3, whose ability to classify the volatile compounds is based on two scales of physicochemical properties: a hydrophilicity/hydrophobicity scale in which the sensors C1 and C2 participate, and an acidity/basicity scale in which one of the sensors C1 and C2 and the sensor C3 participate;

or four sensors, respectively sensors C1, C2, C3 and C4, whose ability to classify the volatile compounds is also based on the two aforementioned scales of physico-chemical properties, the sensors C1 and C2 participating in the first (hydrophilicity/hydrophobicity) scale and the sensors C3 and C4 participating in the second (acidity/basicity) scale.

In accordance with the invention, when the sequence Z is formed by the repetition of an α-amino acid, then this α-amino acid is preferably selected from the 20 α-amino acids commonly known as "standard", namely alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine; it being understood, however, that other α-amino acids such as $N^2$-acetyllysine, $N^6$-acetyllysine, $N^6$-methyllysine, 5-hydroxylysine, 4-hydroxyproline, pyrrolysine, selenocysteine, O-phosphoserine, O-phosphothreonine, O-phosphotyrosine, norleucine or citrulline can also be used.

Moreover, this α-amino acid can be indifferently of L or D configuration and, insofar as it is present in the receptor in the form of a homopeptide, it can be found in this peptide both in the L configuration and in the D configuration.

Advantageously, the α-amino acid is repeated in the sequence Z from 1 to 19 times so that the sequence Z comprises from 2 to 20 times the same α-amino acid.

Preferably, the α-amino acid is repeated in the sequence Z from 3 to 15 times so that the sequence Z comprises from 4 to 16 times the same α-amino acid.

More preferably, the α-amino acid is repeated in the sequence Z from 5 to 9 times so that the sequence Z comprises from 6 to 10 times the same α-amino acid.

In accordance with the invention, the immobilisation of the receptors on the substrate can be carried out by any of the surface functionalisation techniques known to the person skilled in the art such as the physical adsorption, the chemical adsorption, the covalent grafting, the synthesis on a substrate, the deposition of thin layers, the molecular self-assembly, etc.; it being understood that the choice of this technique will depend on the chemical nature of the surface of the substrate.

X can therefore be any functional group or any chemical function (the two expressions being considered as synonyms) allowing immobilising the receptors on the substrate by one of these techniques or the residue of a compound comprising one or more functional groups allowing immobilising the receptors on the substrate by one of these techniques. X can therefore comprise one or more chemical binding functions.

In this regard, it is specified that the term "residue" or "residual portion" of a compound means the portion of the compound which remains on the group Esp (if m is equal to 1) or on the sequence Z (if m is equal to 0) after its covalent bond to the group Esp or to the sequence Z.

Thus, X can in particular be a thiol, amine, hydroxyl, carboxyl, nitrile, selenol, phosphate, sulphonate, silanol, epoxy, vinyl, alkyne or triazide group, or the residue of a compound comprising at least one such group.

Among the aforementioned functionalisation techniques, preference is given, within the scope of the invention, to the molecular self-assembly, in particular because of its reproducibility, in which case X may in particular be:

a thiol group or the residue of a compound comprising, on the one hand, at least one thiol group and, on the other hand, a group allowing its covalent bond to the group Esp or to the sequence Z, if the surface of the substrate is made of gold, platinum, silver, palladium or copper; the compound can in particular be cysteine or N-thiomethyl-glycine; or an amine group or the residue of a compound comprising, on the one hand, at least one amine group and, on the other hand, a group allowing its covalent bond to the group Esp or to the sequence Z, if the surface of the substrate is made of gold, platinum, silver, palladium or copper; the compound can in particular be an amino acid and, in particular, one of the 20 standard α-amino acids; or a silanol group or the residue of a compound comprising, on the one hand, at least one silanol group and, on the other hand, a group allowing its covalent bond to the group Esp or to the sequence Z, if the surface of the substrate is made of glass, quartz, silicon or silica.

In accordance with the invention, m is preferably equal to 1, which means that the group Esp is present, in which case this group can notably be a linear or branched, saturated or unsaturated hydrocarbon group comprising 1 to 20 carbon atoms and optionally one or more heteroatoms, this (these) heteroatom(s) typically being selected from oxygen, nitrogen, sulphur and silicon.

The group Esp can thus be, for example, a divalent alkylene group comprising 1 to 20 carbon atoms, preferably 1 to 12 carbon atoms and, more preferably, 1 to 6 carbon atoms, a residue of an α-amino acid or a chain of residues of one or more α-amino acids (up to a maximum of 20 carbon atoms).

According to a particularly preferred arrangement of the invention:

X is the residue of an α-amino acid, preferably cysteine due to its thiol group, m is equal to 1 and the group Esp is a residue of an amino acid, for example of glycine, or a chain of residues of an α-amino acid, for example, of glycine residues, while the sequence Z is an α-peptide sequence, preferably a hexapeptide.

Thus, the receptors are α-peptides.

As previously indicated, the α-amino acid of the receptor of the sensor C1 is hydrophilic while the α-amino acid of the receptor of the sensor C2 is hydrophobic.

Figure 1:
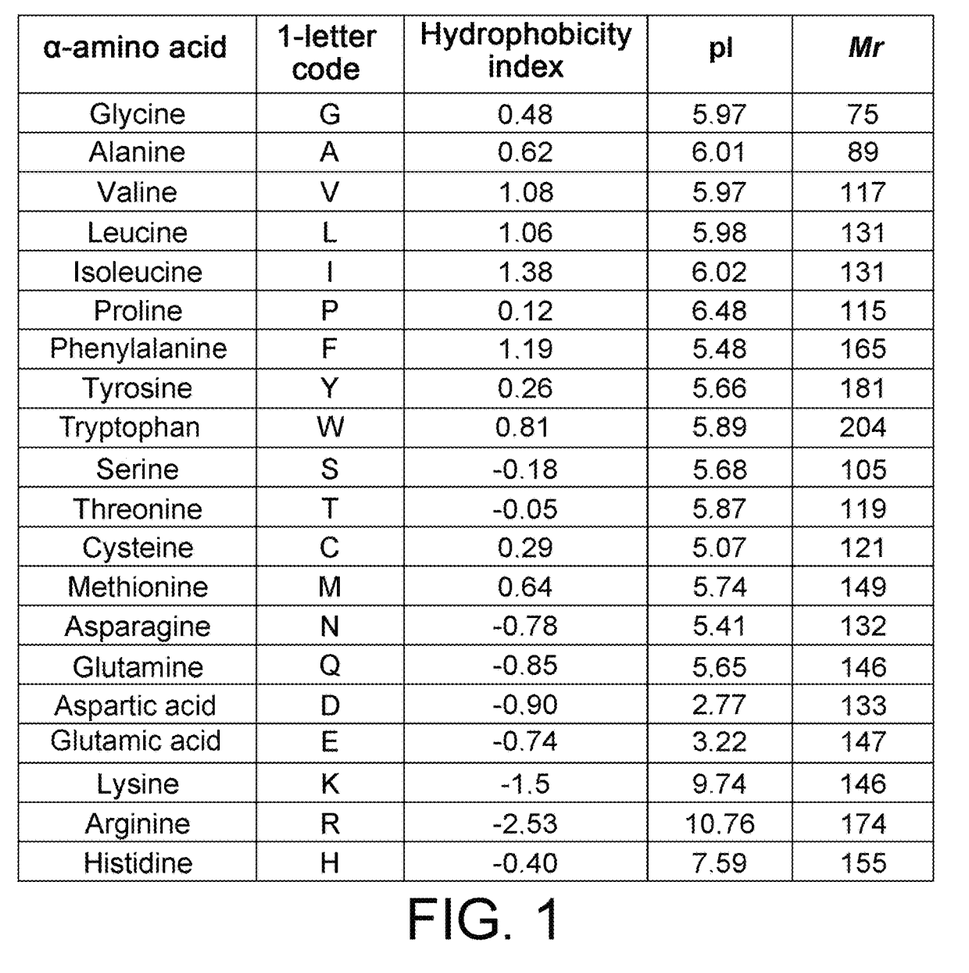
FIG. 1, which is already commented on, is a table showing the hydrophobicity indices according to the scale of R. M. Sweet and D. Eisenberg, the isoelectric points, denoted pI, and the relative molecular weights, denoted Mr, of standard α-amino acids as well as their 1-letter code.

In what precedes and what follows, it is considered that an α-amino acid is hydrophilic when it has a hydrophobicity index less than or equal to 0.26 according to the hydrophobicity scale of R. M. Sweet and D. Eisenberg (*J. Mol. Biol.* 1983, 171, 479-488, hereinafter reference [4]), while an α-amino acid is considered to be hydrophobic when it has a hydrophobicity index higher than or equal to 0.29 according to this same hydrophobicity scale. The hydrophobicity indices, as established by R. M. Sweet and D. Eisenberg for the standard α-amino acids, are shown in FIG. 1 attached in the appendix.

Thus, as shown in this figure, tyrosine, proline, threonine, serine, histidine, asparagine, glutamic acid, glutamine, aspartic acid, lysine and arginine are considered, within the scope of the invention, as being hydrophilic α-amino acids while isoleucine, phenylalanine, valine, leucine, tryptophan, methionine, alanine, glycine and cysteine are considered as hydrophobic α-amino acids.

In accordance with the invention, it is preferred that the α-amino acids of the receptors of the sensors C1 and C2 have relatively remote hydrophobicity indices. The term "relatively remote hydrophobicity indices" means that the sum of the absolute values of these indices, as established by R. M. Sweet and D. Eisenberg, is at least equal to 1.

Thus, for example:
- if the receptor of the sensor C1 has, for hydrophilic α-amino acid, proline whose hydrophobicity index is 0.12 according to the scale of R. M. Sweet and D. Eisenberg, then the α-amino acid of receptor of the sensor C2 will preferably be selected from α-amino acids whose hydrophobicity index is at least equal to 1.06 according to the scale of R. M. Sweet and D. Eisenberg (which is the case of the leucine, valine, phenylalanine and isoleucine), while
- if the receptor of the sensor C1 has, for hydrophilic α-amino acid, asparagine whose hydrophobicity index is −0.74 according to the scale of R. M. Sweet and D. Eisenberg, then the α-amino acid of the receptor of the sensor C2 can be selected from all α-amino acids whose hydrophobicity index is at least equal to 0.29 according to the scale of R. M. Sweet and D. Eisenberg.

As also previously stated, the α-amino acid of the receptor of the sensor C3 and the α-amino acid of the receptor of the sensor C4 have isoelectric points which differ from each other by at least one pH unit and, preferably, by at least two pH units so as to widen the number of volatile compounds likely of being identified by the detection system depending on their acid or base character.

The isoelectric points of α-amino acids are indicated in many books of biochemistry and, alternatively, can be determined by isoelectric focusing (IEF).

By way of example, FIG. 1 attached in the appendix has the isoelectric points, denoted pI, of the standard α-amino acids as taken from the book "Lehninger Principles of Biochemistry", chapter 3, 4$^{th}$ edition, 2004, hereinafter reference [5].

Advantageously, the α-amino acid of the receptor of a sensor of a third series of sensors is aromatic while the α-amino acid of the receptor of another sensor of the third series is aliphatic, these sensors not both belonging to the first series nor to the second series.

Alternatively or in addition, the α-amino acids of the receptors of two sensors of a fourth series of sensors have relative molecular weights, respectively $Mr_1$ and $Mr_2$, which differ from each other by at least 25 g/mol, preferably at least 50 g/mol, these sensors not both belonging to the first series nor to the second series.

Thus, the physicochemical classification of volatile compounds by the electronic nose detection system can be obtained depending on one, or even two additional physicochemical properties of the volatile compounds.

The term "aromatic α-amino acid" means any α-amino acid whose side chain comprises an aromatic group; it being understood that the term "aromatic group" means a group which complies with Hückel's rule and which has therefore a number of delocalised π electrons equal to 4n+2, while the term "aliphatic α-amino acid" means any α-amino acid whose side chain is free of an aromatic group as it has just been defined.

So, for example, histidine, phenylalanine, tyrosine and tryptophan are aromatic α-amino acids while alanine, arginine, asparagine, aspartic acid, cysteine, glutamic acid, glutamine, glycine, isoleucine, leucine, lysine, methionine, proline, serine, threonine and valine are aliphatic α-amino acids.

Like the isoelectric points, the relative molecular weights of the α-amino acids are available in many biochemical books and, alternatively, can easily be determined from the chemical formulas of these α-amino acids.

By way of example, FIG. 1 attached in the appendix shows the relative molecular weights, denoted Mr, of the standard α-amino acids as taken from reference [5].

If the electronic nose detection system comprises the third series of sensors but without the fourth series, then can belong to the third series, either two sensors, respectively sensors C5 and C6, both different from the sensors C1, C2, C3 and C4, or one of the sensors C5 and C6 together with one of the sensors C1, C2, C3 and C4.

Similarly, if the electronic nose detection system comprises the fourth series of sensors, but without the third series, then can belong to the fourth series, either two sensors, respectively sensors C7 and C, both different from the sensors C, C2, C3 and C4, or one of the sensors C7 and C3 together with one of the sensors C, C2, C3 and C4.

Finally, if the electronic nose detection system comprises both the third and the fourth series of sensors, then:
- either the two sensors C5 and C6 or one of the sensors C5 and C6 together with one of the sensors C, C2, C3, C4, C7 or C8 can belong to the third series; while
- either the two sensors C7 and C or one of the sensors C7 and C8 together with one of the sensors C, C2, C3, C4, C5 or C6 can belong to the fourth series.

Table I below shows the different possible configurations.

TABLE I

| | Physicochemical scales | | | |
|---|---|---|---|---|
| Number of sensors | Hydrophilicity/ hydrophobicity | Acidity/ basicity | Aromaticity/ non aromaticity | Mr |
| 3 | C1 and C2 | C3 and (C1 or C2) | | |
| 4 | C1 and C2 | C3 and C4 | | |
| 4 | C1 and C2 | C3 and (C1 or C2) | C5 and (C1 or C2 or C3) | |
| 5 | C1 and C2 | C3 and (C1 or C2) | C5 and C6 | |
| 5 | C1 and C2 | C3 and C4 | C5 and (C1 or C2 or C3 or C4) | |
| 6 | C1 and C2 | C3 and C4 | C5 and C6 | |
| 4 | C1 and C2 | C3 and (C1 or C2) | | C7 and (C1 or C2 or C3) |
| 5 | C1 and C2 | C3 and (C1 or C2) | | C7 and C8 |
| 5 | C1 and C2 | C3 and C4 | | C7 and (C1 or C2 or C3 or C4) |
| 6 | C1 and C2 | C3 and C4 | | C7 and C8 |
| 5 | C1 and C2 | C3 and (C1 or C2) | C5 and (C1 or C2 or C3 or C7) | C7 and (C1 or C2 or C3) |
| 5 | C1 and C2 | C3 and (C1 or C2) | C5 and (C1 or C2 or C3) | C7 and (C1 or C2 or C3 or C5) |
| 6 | C1 and C2 | C3 and (C1 or C2) | C5 and C6 | C7 and (C1 or C2 or C3 or C5 or C6) |
| 6 | C1 and C2 | C3 and (C1 or C2) | C5 and (C1 or C2 or C3 or C7 or C8) | C7 and C8 |
| 7 | C1 and C2 | C3 and (C1 or C2) | C5 and C6 | C7 and C8 |
| 6 | C1 and C2 | C3 and C4 | C5 and (C1 or C2 or C3 or C4 or C7) | C7 and (C1 or C2 or C3 or C4) |
| 6 | C1 and C2 | C3 and C4 | C5 and (C1 or C2 or C3 or C4) | C7 and (C1 or C2 or C3 or C4 or C5) |
| 7 | C1 and C2 | C3 and C4 | C5 and C6 | C7 and (C1 or C2 or C3 |

TABLE I-continued

| | Physicochemical scales | | | |
|---|---|---|---|---|
| Number of sensors | Hydrophilicity/ hydrophobicity | Acidity/ basicity | Aromaticity/ non aromaticity | Mr |
| 7 | C1 and C2 | C3 and C4 | C5 and (C1 or C2 or C3 or C4 or C7 or C8) | or C4 or C5 or C6) C7 and C8 |
| 8 | C1 and C2 | C3 and C4 | C5 and C6 | C7 and C8 |

In accordance with the invention, each of the sensors comprised in the detection system can comprise its own measurement system—or transducer—or share with other sensors a measurement system that is common thereto. In both cases, the measurement system can be any measurement system allowing generating a useable signal during the physicochemical interaction between a compound in the gaseous state and the sensitive part of a sensor and can, in particular, be of the resistive, piezoelectric, mechanical, acoustic or optical type. In other words, the sensors can be resistive, piezoelectric, mechanical, acoustic and/or optical sensors.

Preferably, the sensors are surface plasmon resonance optical sensors, interferometric sensors or else micromachined ultrasonic transducer sensors and, in particular, capacitive micromachined ultrasonic transducer (or CMUT) or piezoelectric micromachined ultrasonic transducer (or PMUT) sensors.

Moreover, it is preferred that the sensors are surface plasmon resonance optical sensors. This type of transduction, which is known per se, generally combines a light source, for example of the LED type, in order to cause a plasmon excitation and a CCD camera to record the signal resulting from the plasmon resonance. As such, it is most particularly preferred that the signals emitted by sensors are tracked in imaging mode which consists in tracking the signal variations of all pixels constituting the image of the used CCD camera.

The substrate consists of a material suitable for the measurement system. Thus, if the measurement is carried out by surface plasmon resonance, then the substrate preferably comprises a glass prism, one face of which is covered with a metal layer, preferably gold or silver, typically 10 nm to 100 nm thick.

The invention also relates to an electronic nose capable of detecting and identifying a set E of compounds likely to be present in a gaseous sample, which electronic nose is characterised in that it comprises a detection system as previously described.

In accordance with the invention, the electronic nose is preferably dedicated to the detection and identification of volatile organic compounds, hydrogen sulphide ($H_2S$) and ammonia ($NH_3$), these compounds possibly being found alone or mixed in the gaseous sample.

In what precedes and what follows, a "volatile organic compound" is defined in accordance with the Directive 1999/13/EC of the European Council of Mar. 11, 1999 under which:

a volatile organic compound is "any organic compound having a vapour pressure of 0.01 kPa (i.e. $9.87 \cdot 10^{-5}$ atm) or more at a temperature of 293.15 K (i.e. 20° C.) or having a corresponding volatility under the particular conditions of use" (cf. paragraph 17 of article 2 of the Directive);

an organic compound is "any compound comprising at least the element carbon and one or more of the following elements: hydrogen, halogens, oxygen, sulphur, phosphorus, silicon or nitrogen, with the exception of carbon oxides and inorganic carbonates and bicarbonates" (cf. paragraph 16 of article 2 of the Directive).

Thus, there are in particular considered as volatile organic compounds, certain saturated or unsaturated acyclic hydrocarbons, such as ethane, propane, n-butane, n-hexane, ethylene, propylene, 1,3-butadiene and acetylene, certain non-aromatic saturated or unsaturated cyclic hydrocarbons, such as cyclopropane, cyclopentane and cyclohexane, certain aromatic hydrocarbons such as benzene, toluene, xylenes and ethylbenzene, certain halogenated hydrocarbons such as dichloromethane, trichloromethane, chloroethane, trichlorethylene and tetrachlorethylene, certain alcohols such as methanol, ethanol, 1-propanol, 2-propanol, ethylene glycol and propylene glycol, certain aldehydes such as formaldehyde, acetaldehyde, propanal and 2-propenal (or acrolein), certain ketones such as acetone, methyl ethyl ketone, 2-butanone and methyl vinyl ketone, certain esters such as methyl acetate, ethyl acetate, isopropyl acetate and isoamyl butyrate, certain ethers such as diethyl ether, n-ethylene glycol butyl ether (EGBE) and 1,4-dioxane, certain acids such as acetic acid and propanoic acid, certain amines such as ethylamine, dimethylamine, trimethylamine, diethylamine and amylamine, certain amides such as dimethylformamide, sulphur compounds such as methyl mercaptan (or methanethiol) and ethyl mercaptan (or ethanethiol), and certain nitriles such as acetonitrile and acrylonitrile.

Other features and advantages of the invention will emerge from the following additional description, which relates to experiments which allowed validating the invention and which is given with reference to the appended figures.

It goes without saying, however, that this additional description is given only by way of illustration of the subject of the invention and should in no case be interpreted as a limitation of that subject.

DETAILED DESCRIPTION OF PARTICULAR EMBODIMENTS

The invention has been validated by the experiments described below.

These experiments were carried out using an electronic nose provided with a detection system comprising:
  on the one hand, an array of 76 sensors whose sensitive parts are arranged on a common substrate and are functionalised by peptide receptors; and
  on the other hand, a surface plasmon resonance (or SPR) optical transducer common to all sensors.

A glass prism covered, on the one faces thereof, with a gold layer (=50 nm thick) was used as a substrate, while 19 different peptides of formula C-G-Z were used as peptide receptors in which:
  C represents the α-amino acid cysteine,
  G represents the α-amino acid glycine, and
  Z represents a hexapeptide sequence consisting of one of the following α-amino acids: alanine, aspartic acid, glutamic acid, phenylalanine, glycine, histidine, isoleucine, lysine, leucine, methionine, asparagine, proline, glutamine, arginine, serine, threonine, valine, tryptophan and tyrosine.

These peptides are designated in the following as well as in FIG. 3 by the 1-letter code of the α-amino acid forming the sequence Z, this code being indicated in the table in FIG. 1.

Thus, for example, the peptide A corresponds to the peptide of formula C-G-A-A-A-A-A-A while the peptide T corresponds to peptide of formula C-G-T-T-T-T-T-T.

All α-amino acids entering into the constitution of peptides are of L configuration.

Each of the sensitive parts of the sensors consists of a self-assembled layer of several molecules of one and the same peptide.

1°) Preparation of the Array of Sensors:

The peptides were dissolved in dimethylsulphoxide (DMSO) at a concentration of 0.1 mmol/L, then the peptide solutions thus obtained were deposited on the gold layer of the substrate using a non-contact microspotter robot (Scienion AG, Germany), at the rate of a few nL per sensitive part.

Each peptide solution was deposited on 4 different areas of the gold layer of the substrate such that each sensor is represented in quadruplicate, to reduce statistical uncertainties on detection.

Moreover, several negative control zones were also created on the gold layer of the substrate, also by means of the microspotter robot, by depositing a few nL of a solution comprising 1H, 1H, 2H, 2H-perfluorodecanethiol in DMSO.

The substrate was then placed for 18 hours in a closed chamber to allow the peptide molecules to be immobilised on the gold layer of this substrate by self-assembly thanks to the thiol-gold chemistry (the thiol being provided by the α-amino acid cysteine of the peptides). Then, the substrate was rinsed to remove the non-immobilised peptide molecules and, finally, dried under a stream of argon.

A substrate was thus obtained comprising 76 sensitive parts likely to interact with volatile compounds as well as several negative control portions.

Figure 2:
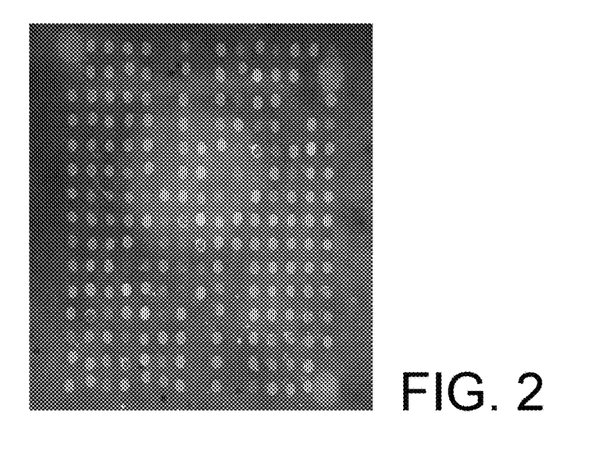
FIG. 2 is a differential image obtained by surface plasmon resonance imaging (or SPRi) which shows the sensitive parts of the array of sensors having served to validate the invention experimentally and in which these sensitive parts are arranged on the surface of a common substrate and are functionalised by 19 different peptides, at the rate of one peptide per sensitive part.

A differential image obtained by SPRi of the sensitive parts of the array of sensors, before any exposure of these sensors to volatile compounds, is illustrated in FIG. 2.

2°) Checking the Functionality of the Array of Sensors:

The array of sensors was exposed to a series of gas samples each comprising a volatile compound belonging to one of the following chemical families: alcohols, carboxylic acids, amines, amides, esters, alkanes, aldehydes, sulphides and aromatics.

Each exposure lasted 10 minutes and a purge of the fluid system for supplying the sensors with gaseous samples was systematically carried out between two consecutive exposures.

The interactions between the sensitive parts of the sensors and the volatile compounds were monitored in real time by SPRi. The data collected by the SPRi images were translated into reflectivity variation values, denoted A % R, which were averaged for each group of 4 identical sensors, then normalised to reduce the impact of the concentration of the organic compounds in the gaseous samples on the collected data.

A database was created from the A % R thus normalised.

This database was analysed by hierarchical clustering.

Hierarchical clustering is a method of data analysis which consists in grouping together the most similar data into classes and separating, on the contrary, those which are dissimilar into distinct classes, and this, depending on a "resemblance criterion". In this case, the resemblance criterion corresponds to the responses of the sensors or, in other words, to the interactions that have occurred between the sensitive parts of the sensors and the volatile compounds to which these sensors have been exposed.

Figure 3:
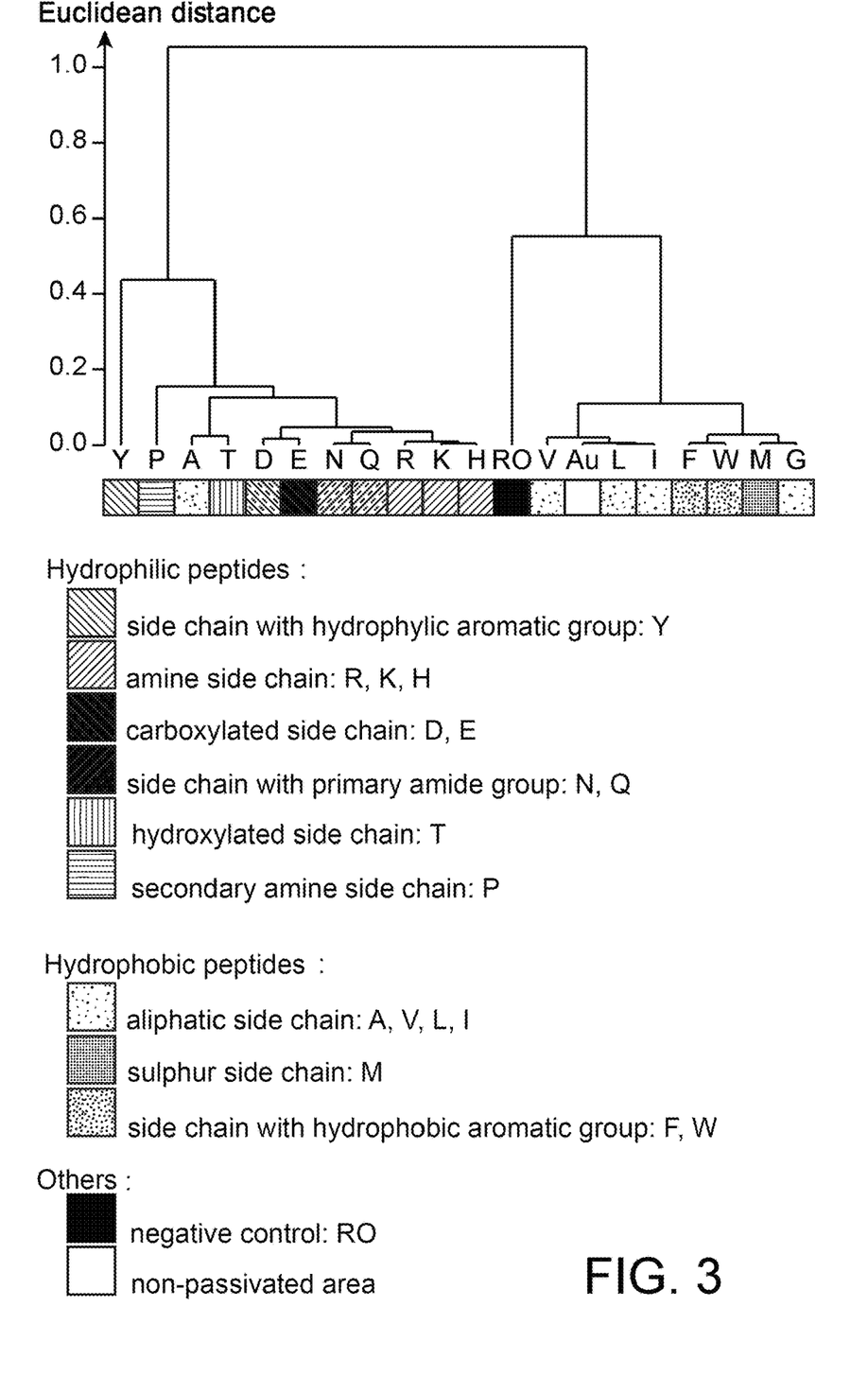
FIG. 3 illustrates, on the one hand, the dendrogram obtained by an analysis by hierarchical clustering of a database constituted from the responses provided by the array of sensors of FIG. 2 during tests aimed at exposing this array of sensors to gaseous samples each comprising a volatile compound, and, on the other hand, a legend of this dendrogram putting in correspondence the peptides forming the sensitive parts of the sensors with the hydrophilic or hydrophobic character of the α-amino acid forming the sequence Z of these peptides.

The dendrogram, or classification tree, resulting from this analysis is illustrated in FIG. 3; on the abscissa axis, the peptides, forming the sensitive parts of the array of sensors (Y, P, A, T, D, E, N, Q, R, K, H, V, L, I, F, W, M and G) are indicated while, on the ordinate axis, the Euclidean distance existing between the different classes of peptides is indicated. The letters "RO" and "Au", also present on the abscissa axis, correspond respectively to the negative controls and to the non-passivated area of the substrate.

Starting from the top of this dendrogram, each branch separates the peptides into different classes, more and more similar the further down the tree is. Thus, the last formed classes group together the peptides which led to the responses of the closest sensors.

As shown in the dendrogram as well as in the legend of this dendrogram, which is also illustrated in FIG. 3, the hydrophilic α-amino acid peptides and the hydrophobic α-amino acid peptides are well separated from each other except alanine while the peptides of the same chemical nature are well grouped.

These results demonstrate that the physicochemical properties of the peptides were not altered during the manufacture of the arrays of sensors.

They demonstrate that peptides of the same chemical nature have similar interactions with volatile compounds belonging to different chemical families and that, conversely, peptides of different chemical nature have different interactions with these compounds. The variety of physicochemical properties of peptides is therefore well represented on the array of sensors and this variety is able to allow an absolute classification of volatile compounds according to several physicochemical scales.

3°) Classification of the Volatile Compounds According to Two Physicochemical Properties:

By reporting the data obtained in point 2°) above on graphs having for abscissa axis and ordinate axis the values presented by α-amino acids for two different physicochemical properties, it was possible to obtain on these graphs an ordering of the organic compounds depending on the physicochemical properties that these compounds themselves have.

Figure 4:
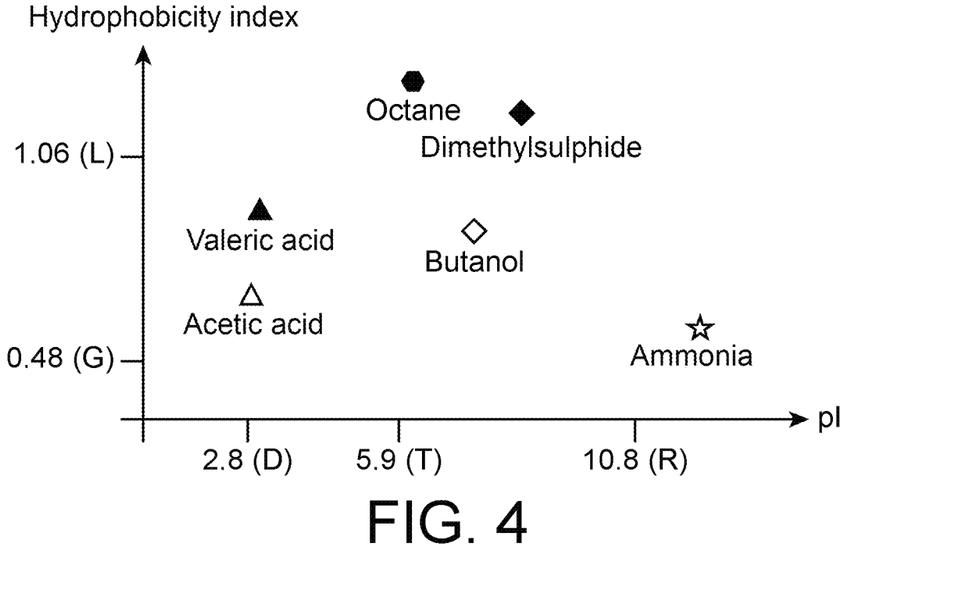
FIG. 4 is a graph illustrating the classification of 6 volatile compounds according to two physicochemical properties having been obtained from a database constituted from the responses provided by the array of sensors of FIG. 2 during tests aimed at exposing this array of sensors to gaseous samples each comprising one of these volatile compounds; on this graph, the abscissa axis corresponds to the isoelectric point, denoted pI, of standard α-amino acids while the ordinate axis corresponds to the hydrophobicity index of these same α-amino acids.

Thus, for example, FIG. 4 shows the ordering obtained for 6 volatile compounds, namely acetic acid, valeric acid, butanol, ammonia, dimethylsulphide and octane, on a graph whose abscissa axis corresponds to the isoelectric point of α-amino acids and whose ordinate axis corresponds to the hydrophobicity index of α-amino acids.

As shown in FIG. 4, each of the volatile compounds is well ordered on the graph and can be distinguished depending, on the one hand, on its acid or base character (corresponding to the abscissa axis) and, on the other hand, on its more or less hydrophobic character (corresponding to the ordinate axis).

An absolute classification of the volatile compounds depending on two physicochemical properties is thus obtained.

4°) Classification of Volatile Compounds According to More than Two Physicochemical Properties:

In order to validate the ability of a detection system in accordance with the invention to allow an absolute classification of odours depending on a wide variety of physicochemical properties, the array of sensors was exposed to a series of gaseous samples each comprising one of the following 9 volatile compounds:

acetic acid ($CH_3$—COOH), hereinafter denoted AcOH,
butanoic acid ($CH_3(CH_2)_2COOH$), hereinafter denoted BTA,
triethylamine ($N(CH_2CH_3)_3$), hereinafter denoted TEA,
trimethylamine ($N(CH_3)_3$), hereinafter denoted TMA,
n-pentylamine ($CH_3(CH_2)_4NH_2$), notée ci-après n-PA,
1,4-diaminobutane ($NH_2(CH_2)_4NH_2$), noté ci-après DAB,
1,5-diaminopentane ($NH_2(CH_2)_5NH_2$), hereinafter denoted DAP,
dimethylsulphide ($S(CH_3)_2$), hereinafter denoted DMS, and
dipropylsulphide ($S(CH_2CH_2CH_3)_2$), hereinafter denoted DPS.

Herein again, each exposure lasted 10 minutes and a purge of the fluid system for supplying the sensors with gaseous samples was systematically carried out between 2 consecutive exposures. The interactions between the sensitive parts of the sensors and the volatile compounds were followed in real time by SPRi and the data collected by the SPRi images were processed as previously described in point 2°) above.

10 exposures of the array of sensors having been carried out per volatile compound, 10 profiles were obtained for each volatile compound from which a database was constituted.

This database was subjected to a principal component analysis (or PCA).

PCA is a method of factorial analysis of data commonly used in the field of electronic noses, in particular for the reduction of dimensions (cf., for example, A. Loufti et al., *Journal of Food Engineering* 2015, 14, 103-111, hereinafter reference [5]). It allows representing a large number of quantitative data according to a plurality of factorial axes, which are linear combinations of the initial variables and which are called "principal components" and denoted PC 1 for the principal component 1, PC 2 for the principal component 2, PC 3 for the principal component 3, etc., and this, while retaining as much information as possible.

Figure 5:
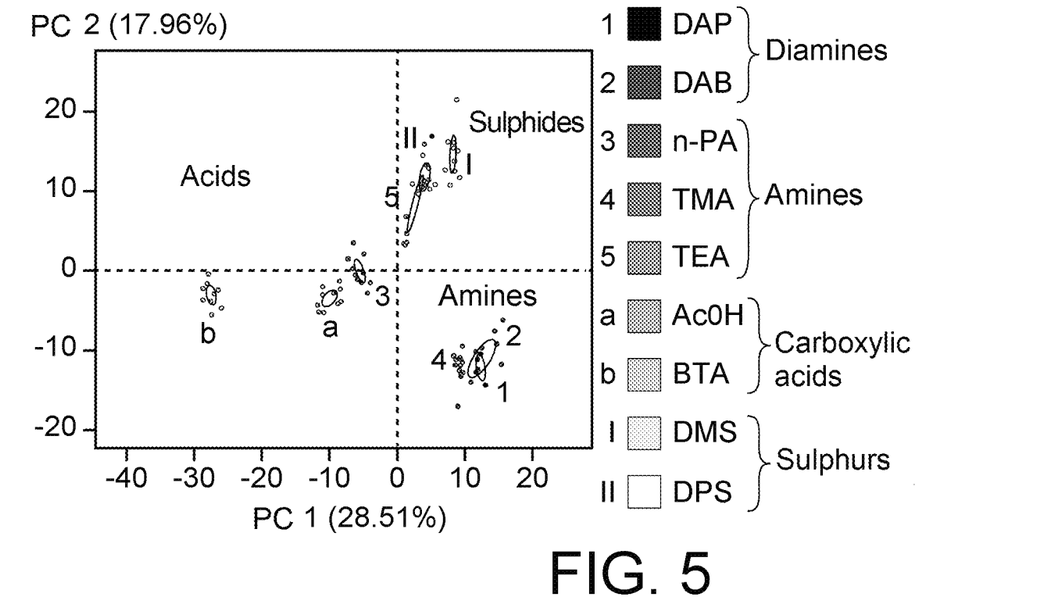
FIG. 5 is the map obtained by principal component analysis 1 and 2, denoted PC 1 and PC 2, of a database constituted from the responses provided by the array of sensors of FIG. 2 during tests aimed at exposing this array of sensors to gaseous samples each comprising a volatile compound; in this Figure, the percentages of variability associated with each of the PC 1 and PC 2 are indicated on the axes.

Applied to the database constituted from the profiles of the volatile compounds to which the array of sensors has been exposed, the PCA has allowed obtaining the map of FIG. 5 which represents the profiles along the axes PC 1 and PC 2 and shows a grouping of the closest profiles and, in particular, of the 10 profiles obtained for each volatile compound, and a separation of the distant profiles into different groups.

Thus, for example, this map shows that, if the profiles of the diamines (DAB and DAP) are well grouped and if the profiles of the dialkylsulphides (DMS and DPS) are also well grouped, however the latter are far from the profiles of the diamines.

The physicochemical properties of the volatile compounds were then correlated with the components PC 1 and PC 2 of the map in FIG. 5. For these correlations, were taken into account:

the n-octanol/water partition coefficient, denoted log P and corresponding to the ratio of the solubilities of a compound in these two solvents; it gives an indication of the hydrophilic or hydrophobic character of the component, the component being, indeed, more hydrophobic and less hydrophilic as its log P is high;

the molar mass, denoted M and expressed in g/mol;

the norm of the dipole moment, denoted p and expressed in Debye (D); the dipole moment is a vector quantity which characterises the state of polarisation of an atomic bond or a molecule; the greater the norm of this vector, the more polar the molecule;

the number of hydrogen bond donor sites, denoted $LH_D$; these are hydrogen atoms bonded to an atom which is more electronegative than the carbon atom, likely to be donated to form a hydrogen bond;

the number of hydrogen bond acceptor sites, denoted LHA; they are electronegative atoms carrying non-binding pairs of electrons, likely to receive a hydrogen bond;

the polar surface, denoted $S_P$ and expressed in Å$^2$; it is defined as the sum of the surface areas of the polar atoms, such as oxygen, nitrogen or sulphur, as well as bonded hydrogen atoms;

the saturated vapour pressure, denoted $P_{sat}$ and expressed in kPa;

the refractive index of the pure compound, denoted n;

the number of carbon atoms, denoted $N_c$, that the compound comprises; and the sum of the electronegativities, denoted IX, of the heteroatoms that the compound comprises ($\chi$=3.5 for O, $\chi$=3 for N; $\chi$=2.5 for S).

The values of these physicochemical properties are presented in Table II below for each of the volatile compounds.

TABLE II

| Compound | logP | M (g/mol) | μ (D) | LH$_D$ | LH$_A$ | S$_P$ (Å$^2$) | P$_{sat}$ (kPa) | n | N$_C$ | Σ$_\chi$ |
|---|---|---|---|---|---|---|---|---|---|---|
| AcOH | −0.2 | 60.052 | 1.7 | 1 | 2 | 37.3 | 1.5 | 1.372 | 2 | 7 |
| BTA | 0.79 | 88.106 | 0.93 | 1 | 2 | 37.3 | 0.057 | 1.398 | 4 | 7 |
| TEA | 1.4 | 101.193 | 0.66 | 0 | 1 | 3.2 | 8.5 | 1.401 | 6 | 3 |
| TMA | 0.3 | 59.112 | 0.612 | 0 | 1 | 3.2 | 187 | 1.3631 | 3 | 3 |
| n-PA | 1.5 | 87.166 | 1.3 | 1 | 1 | 26 | 3.09 | 1.411 | 5 | 3 |
| DAB | −0.9 | 88.154 | 1.26 | 2 | 2 | 52 | 3.1 | 1.457 | 4 | 6 |
| DAP | −0.6 | 102.181 | 1.93 | 2 | 2 | 52 | 0.09 | 1.458 | 5 | 6 |
| DMS | 2.7 | 150.298 | 1.56 | 0 | 1 | 25.3 | 0.86 | 1.4487 | 6 | 2.5 |
| DPS | 0.9 | 62.13 | 1.45 | 0 | 1 | 25.3 | 57 | 1.435 | 2 | 2.5 |

Figure 6:
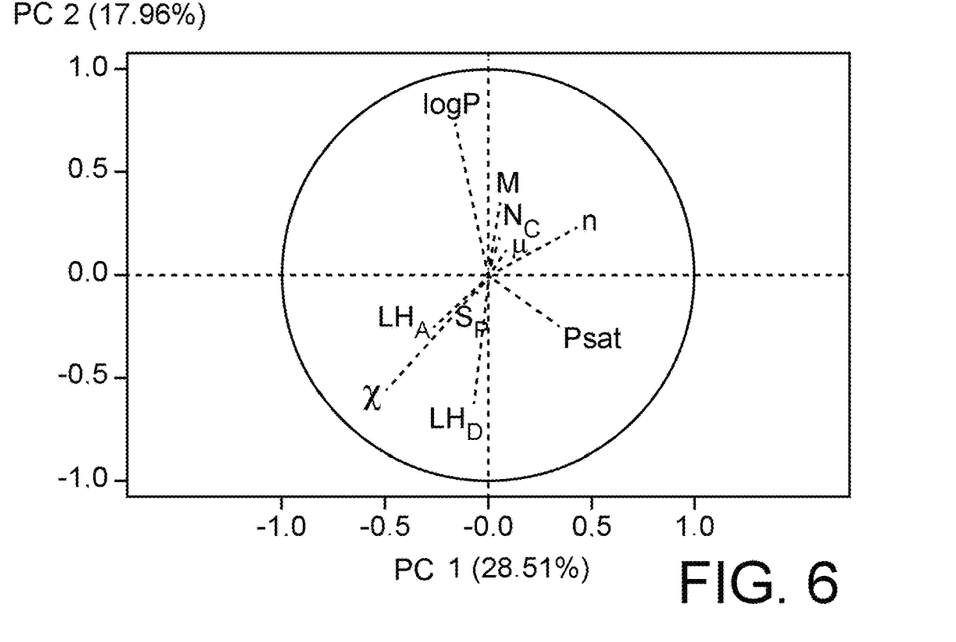
FIG. 6 is a first circle of correlations obtained by principal component analysis 1 and 2, denoted PC 1 and PC 2, of a database constituted from the responses provided by the array of sensors of FIG. 2 during tests aimed at exposing this array of sensors to gaseous samples each comprising a volatile compound and correlation of the physicochemical properties of the volatile compounds tested with these main components.

The circle of correlations shown in FIG. 6 was thus obtained.

In this regard, it is recalled that a circle of correlations is a circle of radius 1 whose two perpendicular diameters represent two principal components, PC 1 and PC 2 in the case of FIG. 6. The descriptors—that is to say the physicochemical parameters of the volatile compounds in the case of FIG. 6—are disposed in this circle and their projection on the principal components gives their correlation coefficient with these components.

Thus, the projection of log P on PC 2 is about 0.8, which indicates a positive correlation between this physicochemical parameter and PC 2. As the correlation is positive, then the higher the log P of a volatile compound, the higher the coordinate of this compound on PC2. The most hydrophobic volatile compounds are therefore found at the top of the map in FIG. 5 and the most hydrophilic are found at the bottom of this map. The array of sensors is therefore capable of differentiating the volatile compounds depending on their hydrophilic or hydrophobic character and of classifying them on a hydrophilicity/hydrophobicity scale.

Similarly, FIG. 6 shows that the LH$_D$ number of hydrogen bond donor sites is also correlated with PC 2. The sensor array is therefore also capable of differentiating the volatile compounds depending on their ability to form a hydrogen bond and of classifying them on a pH scale.

Figure 7:
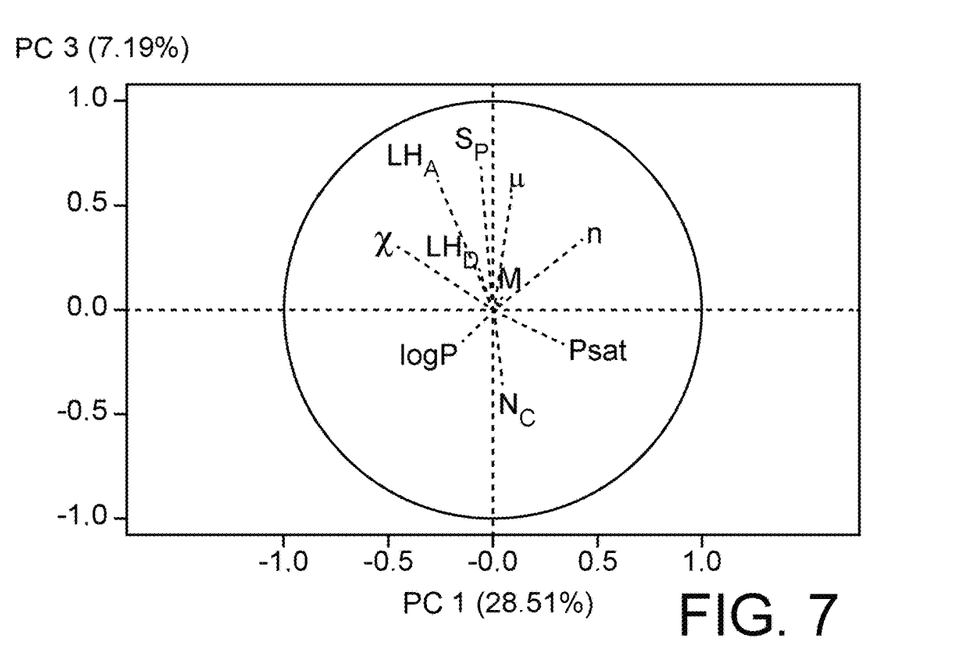
FIG. 7 is a second circle of correlations obtained by principal component analysis 1 and 3, denoted PC 1 and PC 3, of a database constituted from the responses provided by the array of sensors of FIG. 2 during tests aimed at exposing this array of sensors to gaseous samples each comprising a volatile compound and correlation of the physicochemical properties of the volatile compounds tested with these main components.

FIG. 7 illustrates another circle of correlations obtained by correlating the physicochemical parameters of the volatile compounds with the component PC 1 of the map of FIG. 5 and a component PC 3, also obtained by the PCA analysis but not represented on this map. This Figure shows that the norm p of the dipole moment as well as the polar surface $S_p$ are well correlated with PC 3, which means that the array of sensors is capable of differentiating the volatile compounds depending on their polarity and of classifying them on a scale of polarity.

REFERENCES

[1] L. A. Beardslee et al., *Proceedings of the IEEE International Conference on the Micro Electro Mechanical Systems (MEMS)* 2011, 964-967

[2] D. Compagnone et al., *Biosensors and Bioelectronics* 2013, 42, 618-625

[3] S. Brenet et al., *Analytical Chemistry* 2018, 90, 9879-9887

[4] R. M. Sweet et D. Eisenberg, *J. Mol. Biol.* 1983, 171, 479-488

[5] Lehninger Principles of Biochemistry, chapter 3, 4$^{th}$ edition, 2004

[6] A. Loufti et al., *Journal of Food Engineering* 2015, 14, 103-111

What is claimed is:

1. A detection system comprising:

a substrate having a surface;

a plurality of receptors configured to produce a detectable signal when the plurality of receptors physiochemically interacts with at least one volatile compound of a plurality of volatile compounds in a gaseous sample;

three or more sensors having cross-reactivities relative to one or more volatile compounds of the plurality of volatile compounds, each sensor of the three or more sensors comprising a sensitive part disposed on the substrate and functionalised by a receptor of the plurality of receptors and wherein each receptor of the plurality of receptors has a formula X-(Esp)$_m$-Z wherein X is either a functional group for immobilizing a respective receptor onto the surface of the substrate or is a residue of a compound comprising the functional group for immobilizing the respective receptor onto the surface of the substrate, m is 0 or 1, Esp is a spacer arm, and Z is a sequence comprising two or more α-amino acids;

wherein the three or more sensors comprise a first series of sensors and a second series of sensors wherein the first series of sensors comprises a first sensor comprising a first receptor having a first α-amino acid wherein the first α-amino acid is hydrophilic α-amino acid and a second sensor comprising a second receptor comprising a second α-amino acid wherein the second-amino acid is a hydrophobic α-amino acid; and the second series of sensors comprises a third sensor comprising a third receptor comprising a third α-amino acid having a first isoelectric point and a fourth sensor comprising a fourth receptor comprising a fourth α-amino acid having a second isoelectric point wherein the first isoelectric point differs from the second isoelectric point by one or more pH units.

2. The detection system of claim 1, wherein the first isoelectric point differs from the second isoelectric point by two or more pH units.

3. The detection system of claim 1, wherein the two or more α-amino acids are alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine.

4. The detection system of claim 1, wherein the two or more α-amino acids are less than 19 α-amino acids.

5. The detection system of claim 4, wherein X is a thiol, an amine, a hydroxyl, a carboxyl, a nitrile, a selenol, a phosphate, a sulphonate, a silanol, an epoxy, a vinyl, an alkyne or a triazide functional group; or wherein X is a residue of a compound comprising at least one thiol, one amine, one hydroxyl, one carboxyl, one nitrile, one selenol, one phosphate, one sulphonate, one silanol, one epoxy, one vinyl, one alkyne or one triazide group.

6. The detection system of claim 1, wherein m is 1 and the spacer arm is a linear hydrocarbon group or a branched hydrocarbon group, and a saturated hydrocarbon group or an unsaturated hydrocarbon group comprising 1 to 20 carbon atoms and optionally one or more heteroatoms.

7. The detection system of claim 1, wherein X is a residue of an α-amino acid, m is 1, the spacer arm comprises a residue of an α-amino acid or a chain of residues of an α-amino acid, and Z is an α-peptide sequence.

8. The detection system of claim 7, wherein X is a residue of a cysteine and Z is a hexapeptide sequence.

9. The detection system of claim 1, wherein the first α-amino acid and the second α-amino acid have hydrophobicity indices such that a sum of absolute values is 1 or more.

10. The detection system of claim 1, wherein the three of more sensors further comprise a third series of sensors comprising a fifth sensor and sixth sensor, the fifth sensor comprising a fifth receptor comprising a fifth α-amino acid wherein the fifth α-amino acid is an aromatic α-amino acid, the sixth sensor comprising a sixth receptor comprising a sixth α-amino acid wherein the sixth α-amino acid is aliphatic α-amino acid.

11. The detection system of claim 1, wherein the three or more sensors comprise a fourth series of sensors comprising a seventh sensor and eight sensor wherein the seventh sensor comprises a seventh receptor comprising a seventh α-amino acid having a first molecular weight and the eight sensor comprises an eighth receptor comprising an eighth α-amino acid having a second molecular weight wherein the first molecular weight differ from the second molecular weight by 25 g/mol or more.

12. The detection system of claim 1, wherein the three or more sensors are resistive, piezoelectric, mechanical, acoustic or optical sensors.

13. The detection system of claim 12, wherein the three or more sensors are surface plasmon resonance or interferometric optical sensors.

14. The detection system of claim 13, wherein the three or more sensors are micromachined ultrasonic transducer sensors.

15. An electronic nose configured to detect and identify a plurality of volatile compounds in a gaseous sample, the electronic nose comprising the detection system of claim 1.

16. The electronic nose of claim 15, further configured to detect and identify hydrogen sulphide and ammonia.

17. The detection system of claim 4, wherein the two or more α-amino range from 3 to 15 α-amino acids.

18. The detection system of claim 4, wherein the two or more α-amino range from 5 to 9 α-amino acids.

* * * * *